US010645812B2

(12) United States Patent
MacCurdy et al.

(10) Patent No.: US 10,645,812 B2
(45) Date of Patent: May 5, 2020

(54) SYSTEM AND METHODS FOR ADDITIVE MANUFACTURING OF ELECTROMECHANICAL ASSEMBLIES

(71) Applicant: Cornell University, Ithaca, NY (US)

(72) Inventors: Robert MacCurdy, Ithaca, NY (US); Hod Lipson, New York, NY (US)

(73) Assignee: Cornell University, Ithaca, NY (US)

( * ) Notice: Subject to any disclaimer, the term of this patent is extended or adjusted under 35 U.S.C. 154(b) by 516 days.

(21) Appl. No.: 15/305,962

(22) PCT Filed: Apr. 21, 2015

(86) PCT No.: PCT/US2015/026848
§ 371 (c)(1),
(2) Date: Oct. 21, 2016

(87) PCT Pub. No.: WO2016/007207
PCT Pub. Date: Jan. 14, 2016

(65) Prior Publication Data
US 2017/0042034 A1 Feb. 9, 2017

Related U.S. Application Data

(60) Provisional application No. 61/982,172, filed on Apr. 21, 2014.

(51) Int. Cl.
*H05K 1/18* (2006.01)
*H05K 3/28* (2006.01)
(Continued)

(52) U.S. Cl.
CPC .............. *H05K 1/185* (2013.01); *A61B 17/50* (2013.01); *B29C 64/00* (2017.08); *B29C 65/16* (2013.01);
(Continued)

(58) Field of Classification Search
CPC ...... H05K 3/0014; H05K 3/125; H05K 3/284; H05K 3/30; H05K 3/386; H05K 1/185;
(Continued)

(56) References Cited

U.S. PATENT DOCUMENTS 5,189,781 A    3/1993   Weiss et al.
5,203,944 A    4/1993   Prinz et al.
(Continued)

OTHER PUBLICATIONS

MacCurdy, R. and Lipson, H., "Hybrid printing of photopolymers and electromechanical assemblies" presented at 25th Annual Solid Freeform Fabrication Symposium, Aug. 4-6, 2014, Austin, Texas, accessed at semanticscholar.org via Google Scholar on Oct. 28, 2019. (Year: 2014).*

(Continued)

*Primary Examiner* — Joseph S Del Sole
*Assistant Examiner* — Jamel M Nelson
(74) *Attorney, Agent, or Firm* — Valauskas Corder LLC (57) ABSTRACT

A hybrid additive manufacturing approach that incorporates three-dimensional (3D) printing and placement of modules selected from a library of modules to fabricate an electromechanical assembly. By virtue of fabrication of the electromechanical assembly, mechanical properties and electrical properties of the assembly are created. The invention overcomes the material and process limitations of current printable electronics approaches, enabling complete, complex electromechanical assemblies to be fabricated.

27 Claims, 4 Drawing Sheets

(51) Int. Cl.
| | |
|---|---|
| H01L 27/13 | (2006.01) |
| A61B 17/50 | (2006.01) |
| H01L 27/01 | (2006.01) |
| B29C 64/00 | (2017.01) |
| H05K 1/02 | (2006.01) |
| H05K 1/14 | (2006.01) |
| H05K 3/00 | (2006.01) |
| H05K 3/36 | (2006.01) |
| H05K 3/12 | (2006.01) |
| B33Y 10/00 | (2015.01) |
| B33Y 30/00 | (2015.01) |
| B33Y 40/00 | (2020.01) |
| B33Y 80/00 | (2015.01) |
| B29C 65/16 | (2006.01) |
| H01L 21/56 | (2006.01) |
| H01L 21/67 | (2006.01) |
| H01L 23/538 | (2006.01) |
| H01L 25/11 | (2006.01) |
| H01L 25/18 | (2006.01) |
| H01L 25/00 | (2006.01) |
| H05K 1/11 | (2006.01) |
| H05K 3/30 | (2006.01) |
| H05K 1/16 | (2006.01) |
| H05K 3/46 | (2006.01) |
| B29L 31/34 | (2006.01) |

(52) U.S. Cl.
CPC ............. *B33Y 10/00* (2014.12); *B33Y 30/00* (2014.12); *B33Y 40/00* (2014.12); *B33Y 80/00* (2014.12); *H01L 21/56* (2013.01); *H01L 21/67115* (2013.01); *H01L 21/67132* (2013.01); *H01L 23/5384* (2013.01); *H01L 23/5389* (2013.01); *H01L 25/112* (2013.01); *H01L 25/18* (2013.01); *H01L 25/50* (2013.01); *H01L 27/01* (2013.01); *H01L 27/13* (2013.01); *H05K 1/0287* (2013.01); *H05K 1/115* (2013.01); *H05K 1/14* (2013.01); *H05K 3/0014* (2013.01); *H05K 3/125* (2013.01); *H05K 3/284* (2013.01); *H05K 3/30* (2013.01); *H05K 3/368* (2013.01); *B29L 2031/34* (2013.01); *H05K 1/113* (2013.01); *H05K 1/117* (2013.01); *H05K 1/16* (2013.01); *H05K 3/4673* (2013.01); *H05K 3/4697* (2013.01); *H05K 2201/1003* (2013.01); *H05K 2201/10015* (2013.01); *H05K 2201/10022* (2013.01); *H05K 2201/10053* (2013.01); *H05K 2201/10106* (2013.01); *H05K 2201/10166* (2013.01); *H05K 2201/10174* (2013.01); *H05K 2201/10189* (2013.01); *H05K 2201/10636* (2013.01); *H05K 2203/107* (2013.01); *H05K 2203/1327* (2013.01)

(58) Field of Classification Search
CPC ........ H05K 1/14; H05K 1/0287; H05K 1/115; H05K 1/117; H05K 1/113; H05K 1/16; H05K 3/368; H05K 3/4697; H05K 2203/1327; H05K 2203/107; H05K 2201/10106; H05K 2201/10636; H05K 2201/10189; H05K 2201/10174; H05K 2201/10022; H05K 2201/10015; H05K 2201/1003; H05K 2201/10053; H01L 21/56; H01L 21/67132; H01L 23/5384; H01L 23/5389; H01L 25/112; H01L 25/18; H01L 25/50; H01L 27/13; H01L 27/1292; H01L 27/01; H01L 21/67115; B29C 67/0081; B29C 64/00; B29C 65/16; A61B 17/50; B33Y 80/00; B33Y 40/00; B33Y 30/00; B33Y 10/00; B29L 2031/34
See application file for complete search history.

(56) References Cited

U.S. PATENT DOCUMENTS

| | | |
|---|---|---|
| 5,278,442 A | 1/1994 | Prinz et al. |
| 5,281,789 A | 1/1994 | Merz et al. |
| 5,286,573 A | 2/1994 | Prinz et al. |
| 5,301,415 A | 4/1994 | Prinz et al. |
| 5,301,863 A | 4/1994 | Weiss et al. |
| 2004/0100296 A1* | 5/2004 | Ong .................. G01R 31/2884 324/750.3 |
| 2007/0252871 A1* | 11/2007 | Silverbrook ............ B22F 3/008 347/54 |
| 2011/0123794 A1 | 5/2011 | Hiller et al. |
| 2013/0015596 A1* | 1/2013 | Mozeika ................ B25J 9/0084 264/40.1 |
| 2014/0065194 A1 | 3/2014 | Yoo et al. |

OTHER PUBLICATIONS

Knuesel et al., Self-Assembly of Microscopic Chiplets at a Liquid-Liquid-Solid Interface Forming a Flexible Segmented Monocrystalline Solar Cell. Proceedings of the National Academy of Sciences. 107:993-998. 2010.
Ahn et al., Heterogeneous three-dimensional electronics by use of printed semiconductor nanomaterials. Science. Dec. 15, 2006;314(5806):1754-7.
Bernstein et al. Quilt Packaging: High-Density, High-Speed Interchip Communications. IEEE Transactions on Advanced Packaging ( vol. 30, Issue: 4, Nov. 2007 ).
Ray et al., 41.3: Printed Inorganic Light Emitting Diodes for Solid State Lighting. SID Symposium Digest of Technical Papers. 43:562-564. 2012.
Markoff, J., Tiny Chiplets: A New Level of Micro Manufacturing. The New York Times, Apr. 9:D1. 2013.
Palmer JA et al., Realizing 3-D Interconnected Direct Write Electronics Within Smart Stereolithography Structures. ASME 2005 International Mechanical Engineering Congress and Exposition Electronic and Photonic Packaging, Electrical Systems Design and Photonics, and Nanotechnology. pp. 287-293.
Kataria et al., Building Around Inserts: Methods for Fabricating Complex Devices in Stereolithography. Rapid Prototyping Journal 7:253-262. 2001.
De Laurentis et al., Procedure for Rapid Fabrication of Non-Assembly Mechanisms With Embedded Components. ASME 2002 International Design Engineering Technical Conferences and Computers and Information in Engineering Conference, vol. 5: 27th Biennial Mechanisms and Robotics Conference, pp. 1239-1245.
Lopes et al., Integrating stereolithography and direct print technologies for 3D structural electronics fabrication. Rapid Prototyping Journal 18:129-143. 2012.
MacDonald et al.,3D Printing for the Rapid Prototyping of Structural Electronics. IEEE Access 2:234-242. 2014.
Weiss et al., Shape Deposition Manufacturing of Wearable Computers. ed Bourell D (Advanced Manufacturing Design Center and Laboratory for Freeform Fabrication, University of Texas at Austin) vol. 7, pp. 31-38. 1996.
Weiss et al., Shape Deposition Manufacturing of Heterogenous Structures. Journal of Manufacturing Systems 16:239-248. 1997.
Merz et al., Shape Deposition Manufacturing. 1994.
Park et al., Printed Assemblies of Inorganic Light-Emitting Diodes for Deformable and Semitransparent Displays. Science. vol. 325, Aug. 29, 2009.

* cited by examiner

SYSTEM AND METHODS FOR ADDITIVE MANUFACTURING OF ELECTROMECHANICAL ASSEMBLIES

CROSS-REFERENCE TO RELATED APPLICATIONS

This application claims the benefit of U.S. Provisional Patent Application No. 61/982,172 filed Apr. 21, 2014, which is incorporated by reference.

STATEMENT REGARDING FEDERALLY SPONSORED RESEARCH OR DEVELOPMENT

This invention was made with government support under W911NF-11-1-0093 awarded by the Defense Advanced Research Projects Agency (DARPA) and DGE-0707428 awarded by the National Science Foundation (NSF). The government has certain rights in the invention.

FIELD OF THE INVENTION

The invention relates generally to additive manufacturing. More specifically, the invention is directed to a hybrid approach that incorporates three-dimensional (3D) printing and placement of modules selected from a library of modules to fabricate an electromechanical assembly. By virtue of fabrication of the electromechanical assembly, mechanical properties and electrical properties of the assembly are created.

BACKGROUND OF THE INVENTION

Additive manufacturing is increasingly becoming a significant fabrication technique, both in research and industrial settings, applicable to a broad range of applications. Some commercially important additive manufacturing examples include, for example, low-cost rapid tooling manufacturing, low-volume prototype and production runs, medium-volume automotive and aerospace applications, dental restoration, orthopedic implants, custom orthotics, and user-specific artificial limbs. Furthermore, additive manufacturing methods have been used in biomedical research settings to create heterogeneous tissues from individual precursor cell types and to create functional replacements for missing or damaged body parts.

Despite a great deal of effort and the diversity of additive manufacturing techniques, no additive manufacturing process can fabricate high quality electrical interconnections, computational circuits, sensors or actuators in combination with mechanical elements in an integrated component, i.e., electromechanical component.

With Direct-Write electronics ("DW"), or the similar Direct Print ("DP") technique, it has been demonstrated that inkjet printers are capable of fabricating transistors, and have used a combination of inkjet or digital printing and Fused Deposition Modeling ("FDM") or Stereolithography ("SLA") to create electrical circuits within a 3D printed part. One interesting alternative approach uses conventional semiconductor fabrication to create very small semiconductor devices that are subsequently blended with an ink binder. Although electromagnetic actuators fabricated in one process via FDM and DP has been recently demonstrated, it is rudimentary at best.

Despite this progress, enormous challenges must be overcome. Synthesizing electrically conductive materials with volume resistivity similar to bulk metals that can be extruded or deposited in a low-temperature environment (so that is it process-compatible with other materials in the assembly) remains an elusive challenge. The current state of the art, available from various vendors, employs powdered metal inks that are solvent-borne and achieve volume resistivity that is four times (4×) to ten times (10×) larger than bulk metal in the case of silver, and 10× to 50× for copper. These materials require a post-process sintering step, typically by heating to between 80 and 150 degrees Celsius (° C.) in order to achieve the stated resistivity, which can be difficult to integrate with other heat-sensitive components within the assembly. The active devices such as transistors that have been fabricated thus far have lower carrier mobility and lower on-off ratios than similar devices fabricated in silicon.

Printed transistors using complementary logic (p-channel and n-channel devices) have been combined to produce ring-oscillators, inverters and NAND ("Not AND") gates; however low fabrication-temperature organic transistors rely on semiconductor materials that offer dramatically lower charge carrier mobilities than are available via conventional semiconductor fabrication techniques. The large discrepancy between the highest reported electron and hole mobilities for printed polymers for organic transistors imposes additional design trade-offs when fabricating complementary transistor circuits, a key component of logic circuits.

In certain situations carrier mobility impacts the drain current and the transconductance in a field effect transistor. Larger drain currents are desirable for some applications; however, as a consequence of lower mobility and larger oxide thickness, printed organic transistors typically offer drain currents that are several orders of magnitude smaller than conventional devices. It has been found that wider channels can be used to increase drain current, though this is usually accompanied by increased leakage. Resolution limitations of current printable electronics techniques impose a feature-size penalty of nearly three orders of magnitude, relative to conventional semiconductor fabrication techniques, which limits the amount by which the channel length can be reduced.

Larger transistor feature sizes lead to increased parasitic capacitances at each transistor, reducing their switching speed. Lower transconductance also limits switching speed; the propagation delay of recent fast organic transistors is at least three orders of magnitude slower than conventional transistors, limiting their use to relatively simple logic circuits since this delay accumulates with each cascaded logic cell. Printed organic semiconductors sacrifice endurance relative to conventionally fabricated circuits, with published shelf- and operating lifetimes ranging from several weeks to two years.

Conductor quality in printed electronics is impaired by incompatible material processing requirements. Low-resistivity base materials and narrow traces with high current-carrying capacity are desired In order to achieve favorable conductivity, electrically conductive materials are used. Electrically conductive materials including conductive materials that can be inkjet-printed or extruded are referred to as "inks". These inks typically require a post-print curing or sintering step that entails heat-treating at temperatures ranging from 125 to 500° C. for an extended period of time. Since this range exceeds the glass-transition temperature of most common polymers used in additive manufacturing, the sintering step can cause other materials in the part to melt or degrade.

To circumvent this problem, alternative sintering techniques have been developed based on chemical reactions, resistive heating, plasma, photonic energy, and radio-frequency heating. Recent results compatible with low-temperature polymer substrates demonstrate conductor resistivity of 2-10× bulk via pulsed Xenon lamps, and pulsed-laser, though integration of these methods with structural additive manufacturing materials has not been demonstrated. Reactive silver inks have been shown to yield traces with conductivity nearly equal to bulk silver after 15 minutes of sintering at 90° C., though material costs may limit this approach.

A commercially available method for creating electrical conductors on the surface of plastic parts, known as Laser Direct Structuring ("LDS"), uses a laser to ablate the thermoplastic substrate where conductive traces are desired; organic-metallic additives in the plastic are activated during this process, leaving behind a surface that can be plated during successive wet metallization steps. However, like the other methods mentioned above, LDS creates electrical traces only on the surface of a part and limitations in achievable trace thickness impose constraints on current-carrying capacity despite continuing improvements in material resistivity.

An alternative fabrication approach, Shape Deposition Manufacturing ("SDM"), circumvents material and process compatibility issues by embedding prefabricated components into an assembly as it is being fabricated. This concept has been demonstrated by embedding complete assembled circuit boards as well as discrete components; these components are interconnected with embedded wires or printed conductors subject to the limitations discussed above. At a smaller scale, individual pieces of prefabricated semiconducting material referred to as "chiplets", have been self-assembled to form functional arrays of devices over large scales, including roll-roll manufactured LED sheets, and flexible arrays of chip-scale solar cells. When fabricated with high-speed electrical interconnects on their edges, individual chiplets can be interconnected to form larger composite circuit "Quilts". A related approach also decomposes the problem into separate high-temperature fabrication steps using conventional micro-fabrication tools, followed by a low-temperature assembly process based on transfer printing.

Existing manufacturing methods exist that embed components; however these methods rely on special-purpose embedding of particular components for specific designs. For example, U.S. Pat. No. 5,278,442 to Prinz et al. discloses electronic components formed in place by incremental material build-up of thin layers. At least one mask is used per layer to form electronic components made of conductors such as gold and copper, insulators such as ceramic materials and possibly semiconductors, all of which are applied by thermal deposition spray using a thermal deposition spray.

Another example of an existing manufacturing method that embeds components is described in U.S. Pat. No. 5,301,415 to Prinz et al., which forms three-dimensional objects by applying segments of complementary material and deposition material so as to form layers of material. Selected segments of material are then shaped after one or more segment is formed. In this manner, layers of material form a block containing the object made of deposition material and surrounded by complementary material, which may subsequently be removed.

As further described in U.S. Pat. No. 5,286,573 to Prinz et al., the support structure has a melting point lower than the melting point of the deposition material so that the support structure can be removed by a melting process.

With all of the above described methods, embedded components are printed or shaped within a complementary material, which may ultimately be removed. These components are specific to the desired application of the assembly. Though multiple additive material deposition techniques have been developed to address diverse users, existing techniques fail to address three critical requirements that electromechanical printers must satisfy. First, existing methods produce components with electrical performance that is inferior to conventionally produced electrical components by several orders of magnitude. Second, existing methods are incapable of combining the diverse materials required for complex, integrated electromechanical systems. Thus, there is a need for general-purpose, scalable manufacturing methods that employ a library of pre-fabricated modular components that are universal in manufacturing a variety of assemblies. Third, existing techniques that embed components do not contemplate or demonstrate a modular, general-purpose system. Instead they embed specific pre-fabricated components that are unique to each intended end-use or printed/assembled design. This limitation makes existing methods incapable of addressing the need for a general-purpose electromechanical 3D printer. The invention satisfies these needs.

SUMMARY OF THE INVENTION

The invention overcomes the material and process limitations of current printable electronics approaches, enabling complete, complex electromechanical assemblies to be fabricated.

The few available tools that integrate electrical and mechanical design into an electromechanical design environment do so by relying on the printed circuit board as a natural interface between the electrical and mechanical functions of the assembly. In making this choice, the traditional separations between electrical and mechanical design are entrenched: the circuit board has no mechanical functionality apart from the space that it occupies, and the mechanical components merely provide a physical substrate for the electronics. High-performance 3D-printable electrical components cannot be fabricated by existing additive manufacturing tools.

The invention is directed to finished parts with complex electromechanical properties that can be simulated, designed and fabricated. Specifically, the invention relates to an additive manufacturing process that fabricates high quality electrical interconnections, computational circuits, sensors or actuators in combination with mechanical elements in an integrated electromechanical assembly.

The invention is directed to a hybrid approach that incorporates three-dimensional (3D) printing and placement of modules selected from a library of modules to fabricate an electromechanical assembly with mechanical and electrical functionality comparable to conventionally produced planar printed circuit boards. 3D printing processes includes a variety of methods including, for example, Inkjet, Fused Deposition Modeling ("FDM"), Stereolithography ("SLA"), Drop-On-Demand/Inkjet, or Powder-bed/Binder-jetting, to name a few. Additive processes are used in 3D printing in which successive regions of material are laid down under computer control creating an object of any shape or geometry, and may be produced from a 3D model or other electronic data source. A component placement system is used to position one or more module components within the object during printing.

According to one embodiment of the invention, module components used in fabrication include both electrical properties—also referred to as "electrical functionality"—and mechanical properties—also referred to as "mechanical functionality"—with each module component treated as an inherently electromechanical object. This becomes increasingly true as the module size decreases and the percent volume occupied by modules within the assembly increases. Modules with unique physical properties expand the variety available to designers.

The invention goes beyond previous system and methods that employ either a single module type, or are not modular at all, requiring components specific to the desired assembly design to be loaded into a printer. In contrast, the invention relies on a modular design philosophy: a small set of modules with generic electrical and/or mechanical functionality can be combined, in large numbers if required, to yield the desired performance.

Specifically, the invention incorporates different module types—such as a microcontroller module, resistor module, capacitor module, diode module, transistor module—that may be mechanically similar, but have distinct electrical functionality, into a 3D-printed assembly as it is being fabricated. Each module may include electrical functionality, mechanical functionality, or both. In one embodiment, the invention employs continuous material deposition via inkjet to create the portions of the assembly that require mechanical functionality, and pick-and-place manipulators to deposit modules wherever electromechanical functionality is required.

The system and methods of the invention may be used to fabricate any type of assembly, for example one that is activated when a button is depressed on the surface of the assembly. The system and methods of the invention may also be used to fabricate assemblies that exploit the programmability provided by a particular module.

Design tools such as 3D Computer Aided Design ("CAD") systems are used to create an assembly. The assembly is created to incorporate modules by using volumes of space, or voids. A printer creates regions from conventional inkjet material and modules are positioned within the voids of the region portion created by the printer. If necessary, heating is applied to fuse modules on adjacent regions together or to fuse modules to the regions themselves. This process continues until the assembly is complete.

According to the invention, the number of unique combinations of module components positioned within a material is endless. The combination and position of module components determine the mechanical and electrical properties of the electromechanical assembly.

In a specific embodiment, the invention incorporates a limited repertoire of prefabricated modules with inkjet-deposited photopolymers to create assemblies that incorporate complex mixed-signal circuits with state of the art performance. This modular technique is scalable, allowing a single machine to produce finished parts with diverse functionality without being reconfigured and immediately commercialized using available technology.

One advantage of the invention, in contrast to related work that embeds special-purpose circuit boards within a printed assembly, the invention utilizes a small library of general-purpose modules with atomic functionality. By controlling the position and orientation of these parts within an assembly, new electrical circuits can be fabricated without re-designing individual circuit boards.

Electrical components are commercially available in thousands of distinct physical packages. This heterogeneity, while offering design flexibility, presents a challenge to methods that directly embed commercially-available electronic packages, as it requires package-specific descriptor libraries for each device envelope and footprint to be developed.

Another advantage of the invention is that it reduces designer workload by intentionally restricting the availability of components to a predetermined set that have been fully specified, facilitating circuit modeling via existing tools and eliminating the need to develop new electrical package descriptions.

Component heterogeneity also presents challenges for pick-place apparatus. Though conventional automated placement tools are flexible enough to accommodate a variety of component packages, these tools must be manually configured before each production run, with operators loading in the particular collection of components that will be used for the design. This overhead currently limits low-volume printed circuit board assembly; most commercial assembly providers employ manual assembly at very low production volumes to circumvent the setup cost. Since single-unit or ultra-low-volume production runs are a key motivation for using additive manufacturing, setup costs must be minimized, which argues for restricting the allowable components to a small set that can be permanently maintained within the printer.

In one embodiment of the invention, the allowable module components are restricted to a small set that can be permanently maintained within the printer through a library of modules. The library houses prefabricated modules with the same configuration in terms of size and shape, but differ with respect to electrical functionality and/or mechanical functionality. The modules in the library can support a variety of electrical functionality, such as currents to at least 1 Amp (A), several orders of magnitude larger than known comparable printed-electronics methods, and leverage decades of progress in semiconductor fabrication. Complementary metal-oxide-semiconductor (CMOS) processing steps for integrated circuits may be used to allow digital logic to be embedded within each module.

Methods that interconnect embedded commercial components with printed conductors are limited by conductivity (limited by conductor geometry and material volume resistivity), and process temperature, while those that employ printed semiconductors sacrifice drain current, on/off ratio, and switching speed. In contrast, electrical connectivity according to the invention is achieved through direct connections between adjacent modules, yielding composite conductors that are nearly identical to conventional copper traces.

The invention and its attributes and advantages will be further understood and appreciated with reference to the accompanying drawings.

BRIEF DESCRIPTION OF THE DRAWINGS

The preferred embodiments of the invention will be described in conjunction with the appended drawings provided to illustrate and not to the limit the invention, where like designations denote like elements, and in which.

DETAILED DESCRIPTION

The invention demonstrates a capability that is impossible with contemporary electronics printing methods, and would require a costly electrical and mechanical design cycle, along with special-purpose tooling if it were produced following conventional electromechanical fabrication practice.

The invention is directed to a hybrid approach that incorporates three-dimensional (3D) printing and placement of modules selected from a library of modules to fabricate an electromechanical assembly with both mechanical functionality and electrical functionality comparable to conventionally produced planar printed circuit boards.

Figure 1:
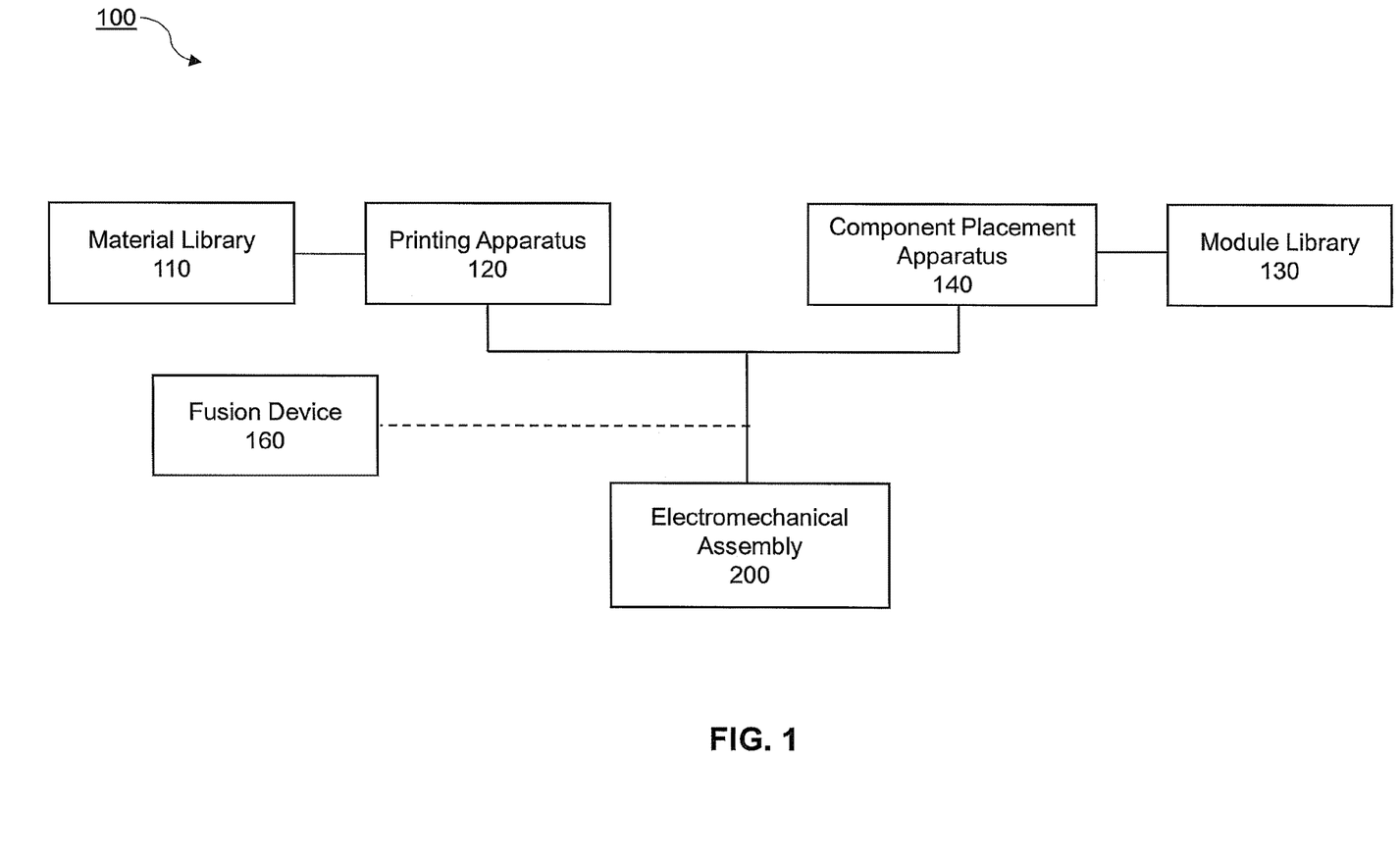
FIG. 1 illustrates a block diagram of an exemplary system for fabricating an electromechanical assembly according to the invention.

FIG. 1 illustrates a block diagram of an exemplary system 100 for fabricating an electromechanical assembly according to the invention. The system 100 facilitates a hybrid approach that incorporates devices such as a printing apparatus 120 and a component placement apparatus 140 to fabricate an electromechanical assembly 200. The printing apparatus 120 may include any type of printing functionality such as a 3D printing machine. The component placement apparatus 140 may include any type of selection and placement of components such as a high speed pick-and-place machine including with parallel pick-and-place techniques, or other similar techniques. Parallel fabrication methods may be used to exploit the mechanical regularity of the modules to manipulate entire regions simultaneously.

The printing apparatus 120 may access a material library 110 to obtain the material for printing. The material library 110 may include one or more different types of materials that may be printed, for example, photopolymers or thermoplastics, although any type of material may be used that is capable of being deposited by a 3D printing machine, including for example an inkjet process.

The component placement apparatus 140 may access a module library 130 for selection of module components for positioning within the material printed by the printing apparatus 120. The module library may include different generic, prefabricated module components that vary in electrical functionality and/or mechanical functionality. Representative module components are more fully described in reference to FIG. 2 and FIG. 3 below.

In certain embodiments, a fusion device 160 such as a laser sintering machine may fuse the module components to one another in order to form an electrical connection in order to realize electrical properties. It is also contemplated the fusion device 160 may be used to fuse the module components to the material printed by the printing apparatus 120.

In addition to the module components including mechanical properties and/or electrical properties, the combination of material printed from the printing apparatus 120 and module components selected and placed by the component placement apparatus 140 create the electromechanical assembly 200 with both mechanical properties and electrical properties. Mechanical properties include, for example, stiffness, strength, stress, and strain. Electrical properties include any control of electrical energy such as circuits including, for example, resistivity and conductivity.

Figure 2:
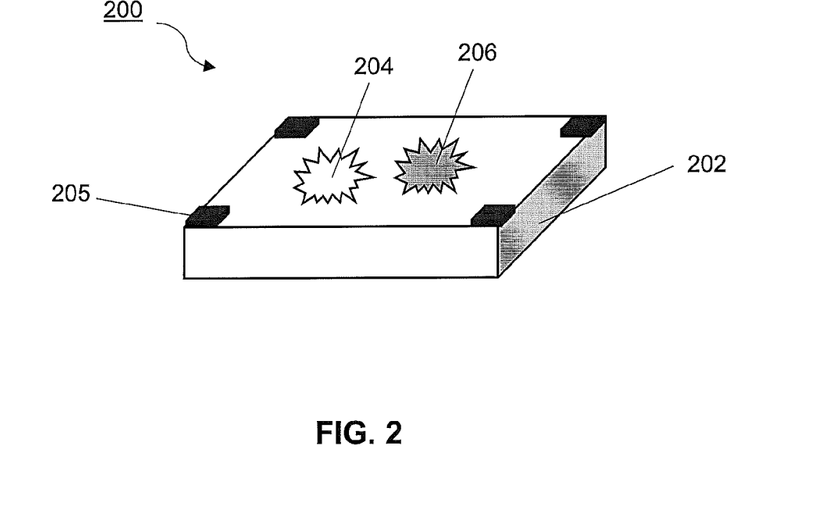
FIG. 2 illustrates a perspective view of a module component according to the invention.

FIG. 2 illustrates a perspective view of a module component 200 according to the invention. Each module component 200 comprises a tile element 202 comprising a plurality of surfaces. As illustrated, the tile element 202 is generally square in shape, but any shape is contemplated. For example, the tile element may be circular, spherical, or rectangular parallelepiped, to name a few examples. In one specific embodiment, the tile element 202 is a 3 millimeter (mm) square shape with a thickness of 0.9 millimeters (mm) in order to allow easy scaling to higher levels of additive manufacturing. However, the invention is applicable to module components of any size that are amenable to manipulation using a component placement apparatus.

The tile element 202 includes one or more pads 205 that may be used for connections. The pads 205 are shown on a top surface of the module component 202, but pads may also be located on the surface opposing the top surface. As an example, pad on the top surface may be connected to pads on the bottom surface by a via in each pad. It is also contemplated that the pads may provide programming signals, enabling the printing apparatus 120 (FIG. 1) to individually program each module.

An electrical element 204 and/or a mechanical element 206 may be either positioned on a surface of the tile element 202 or within a surface of the tile element 202 in order to create functionality/properties—electrical/mechanical—for the prefabricated module component 200 for entry into the module library 130 (FIG. 1). The surface opposing the surface that includes the electrical element 204 and/or a mechanical element 206 is generally planar. Electrical elements 204 control electrical energy and may include, for example, 2-way connect, 4-way connect, crossover connect, resistor, capacitor, inductor, diode, transistor, switch, and microcontroller, as seen schematically in FIG. 3. Mechanical elements 206 control mechanical energy and may include any working or moveable function, such as a gripper or robot effector.

Figure 3:
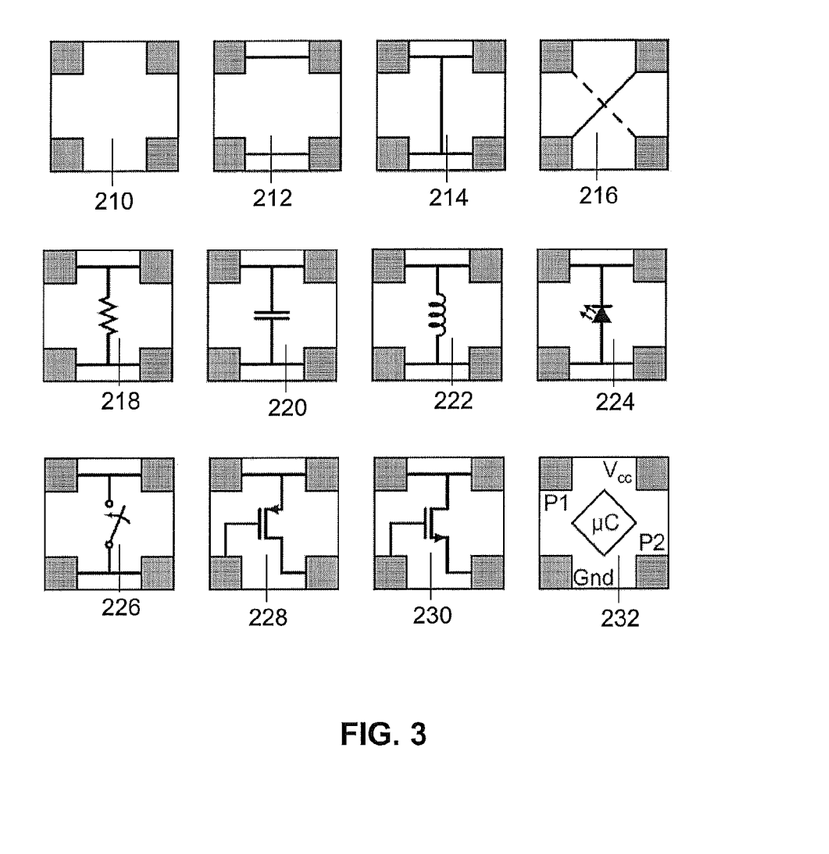
FIG. 3 illustrates schematic diagrams of select module components according to the invention.

FIG. 3 illustrates schematic diagrams of select module components 204 according to the invention. As shown more specifically in FIG. 3, a blank module component 210 does not include an electrical element or mechanical element. Module component 212 illustrates a 2-way connect. Module component 214 illustrates a 4-way connect. Module component 216 illustrates a crossover connect. Module component 218 illustrates a resistor. Module component 220 illustrates a capacitor. Module component 222 illustrates an inductor. Module component 224 illustrates a diode, specifically a Light Emitting Diode ("LED"). Module component 226 illustrates a switch. Module component 228 and module component 230 illustrate transistors, specifically a p-channel field-effect transistor ("P-FET") and a n-channel field-effect transistor ("N-FET"), respectively. Module component 227 illustrates a microcontroller.

The system and methods according to the invention were used to fabricate a 2.5-D interconnection in which neighboring modules on the same region rely on offset modules above or below for electrical connections. Electrical circuits are formed by creating chains of modules on 2 or more regions. This approach allows new modules to be added to an assembly at any vacant location, avoiding interference fits that would otherwise require high-precision placement or large mating forces. This 2.5-D interconnection strategy is one of several contemplated topologies; other strategies compatible with this invention include full 3D interconnections (in-plane connections between modules).

It is contemplated that all modules may share the same mechanical interface, for example 3 mm square, 0.9 mm thick, with four square pads on the top and bottom. These dimensions are incidental, as they are driven by the printed circuit board fabrication methods employed to produce the modules. The invention is equally applicable to smaller modules produced via micro-fabrication, with the added capability of embedding the electronic functionality within, rather than on top of, each module.

With the exception of the blank module 210 of FIG. 3), the topside pads of each module are connected to their corresponding bottom side pads by a via in each pad. Eight of the module types implement carrier boards for commercially available electronic components, breaking out disparate package connections into a common format. While some modules support electrical elements 204 (FIG. 2) positioned on or within their top side, certain modules may not have components on or within their bottom side in order to facilitate automated manipulation. In alternate embodiments, the electrical elements 204 and/or mechanical elements 206 may be positioned on or within one or more surfaces of the module component 200.

In particular embodiments, the FET modules 228, 230 support drain currents in excess of 3 A and can be used with signals as fast as 10 Megahertz (MHz). The microcontroller module 232 employs an Atmel ATtiny10 that contains 1 kB of code space, 32 bytes of RAM, an analog to digital converter, internal oscillators, and timer circuitry. This module's pads may also provide programming signals, enabling the printer to individually program each microcontroller module as it is placed.

Figure 4:
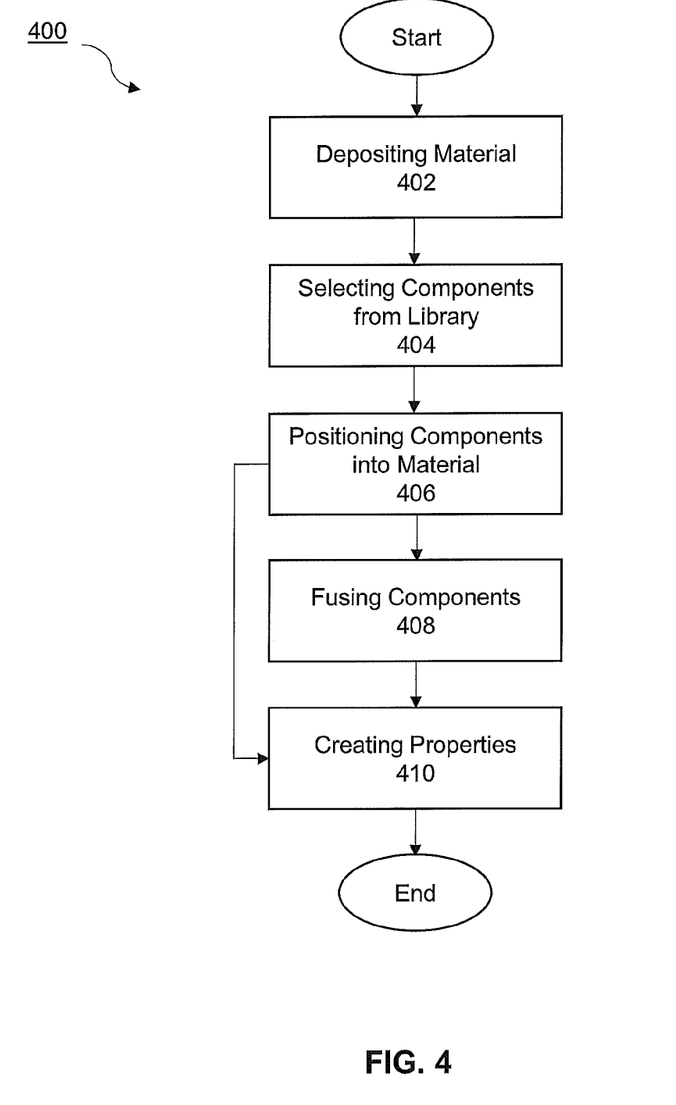
FIG. 4 illustrates a flow chart of an exemplary method for fabricating an electromechanical assembly according to the invention.
Figure 5:
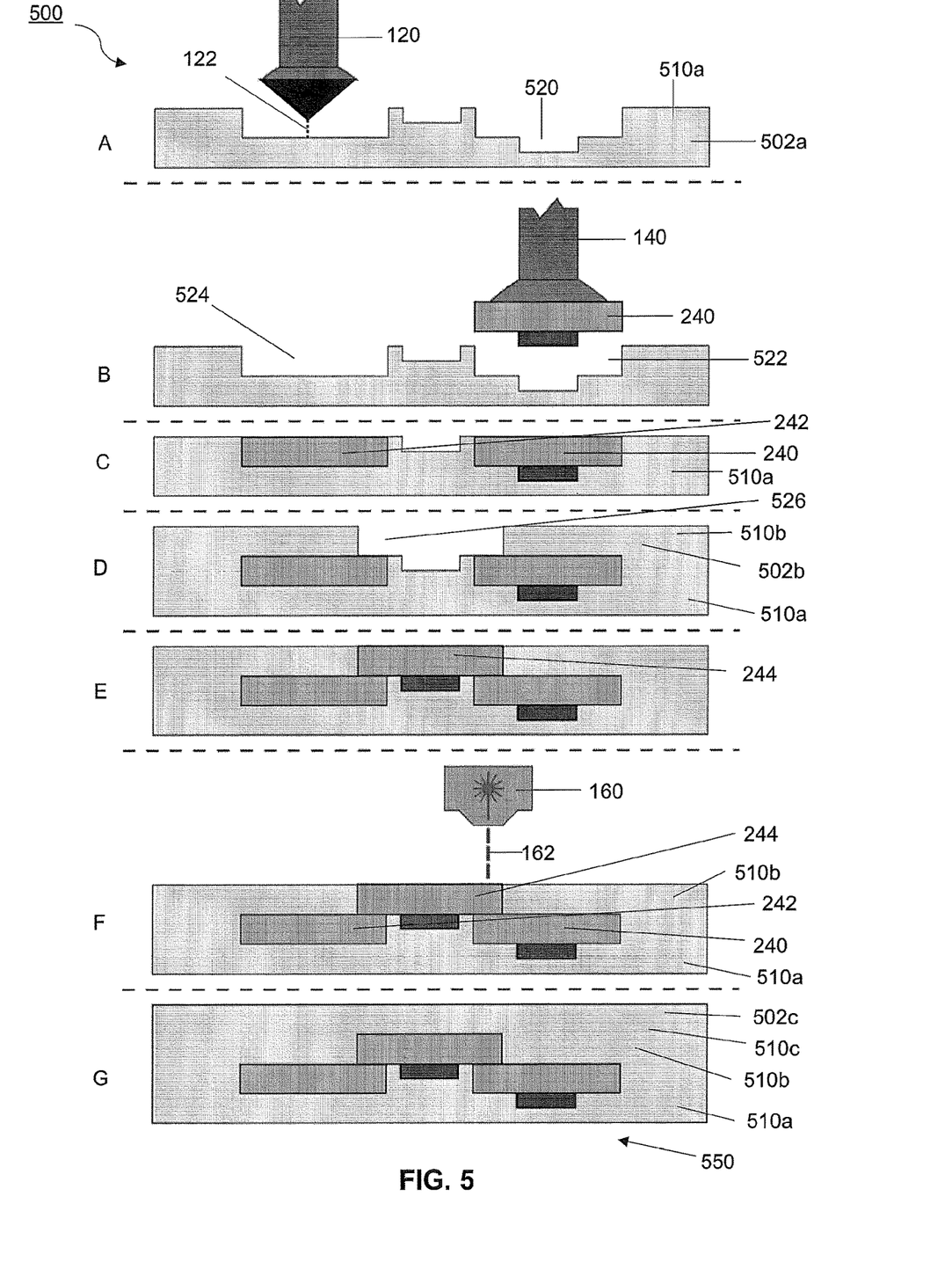
FIG. 5 illustrates a graphic representation for fabricating an electromechanical assembly according to the invention.

FIG. 4 and FIG. 5 illustrate exemplary methods for fabricating an electromechanical assembly according to the invention. Specifically, FIG. 4 is a flow chart and FIG. 5 is a graphic representation.

As shown in FIG. 4 at step 402, material is selected and deposited into a plurality of stacked regions, each successive region positioned on top of the previous region. At step 404, module components are are selected from a library of modules. The module components are positioned into the material at step 406. In certain embodiments, the module components may be fused together or fused to the material as shown in step 408. At step 410, mechanical properties and electrical properties are created by virtue of fabrication of the electromechanical assembly.

FIG. 5 illustrates a graphic representation for fabricating an electromechanical assembly. As shown in FIG. 5, step "A" is directed to a first device 120 depositing material 122, for example using an inkjet process, into a plurality of stacked regions 502a with each successive region positioned on top of the previous region. The plurality of stacked regions 502a forms a base region portion 510a including one or more void elements 520 as constructed by the material 122 such as a photopolymer material.

As shown by step "B", a second device 140 such as a high speed pick-and-place machine, selects a module component 240 from the library of module components and positions the module component 240 in one of void elements 522, 524.

Step "C" illustrates both module components 240, 242 positioned within the base region portion 510a. Step "D" illustrates a second plurality of stacked regions 502b forming a top region portion 510b deposited by the inkjet 3D printing machine 120. The top region portion 510b encapsulates all or a portion of the module components 240, 242 while forming void element 526.

As shown by step "E", the high speed pick-and-place machine 140 selects module component 244 and positions it in void element 526.

In certain embodiments, a fusion device 160 as shown in step "F", such as a laser sintering machine, applies heat in the form of a laser beam 162 in order to fuse the module components 240, 242, 244 to one another. The laser sintering machine 160 may also apply heat to fuse the module components 240, 242, 244 to a region portion 510a, 510b.

As shown in step "G", material is deposited into a third plurality of stacked regions 502c with each successive region positioned on top of the previous region. The plurality of stacked regions 502c forms a second top region portion 502c that encapsulates all of the module components 240, 242, 244 forming an electromechanical assembly 550. By virtue of fabrication of the electromechanical assembly 550, mechanical properties and electrical properties of the assembly are created.

The system and methods of the invention may be used to fabricate any type of assembly, for example an LED keychain light, activated when a button is depressed on the surface. The system and methods of the invention may be used to fabricate assemblies that exploit the programmability provided by a microcontroller module.

For example, a microcontroller module may be programmed to create specific pulse-trains such as those that correspond to the on and on-off pulses in a particular infra-red (IR) remote control protocol. These pulses can be used to turn an IR LED on and off, controlling a remote device. Another example includes the play/pause, jog forward, jog backward, volume up and volume down functions, creating a 5-channel IR remote control. Each of the assemblies employ the inkjet-printed material as a supportive structure, and the remote utilizes a flexible material around the buttons that allows motion during button-press events.

Another example of an assembly incorporates a LED into a structure that has full electromechanical functionality. Inkjet-produced areas can incorporate components such as rack-and-pinion connections, pin-in sockets, captive hinges, and springs. When one component is activated, one or more other components may be activated. For example, when a component on a gripper is activated, the gripper arms open and an internal switch closes, activating an illumination component.

While the disclosure is susceptible to various modifications and alternative forms, specific exemplary embodiments of the invention have been shown by way of example in the drawings and have been described in detail. It should be understood, however, that there is no intent to limit the disclosure to the particular embodiments disclosed, but on the contrary, the intention is to cover all modifications, equivalents, and alternatives falling within the scope of the disclosure as defined by the appended claims.

The invention claimed is:

1. A method for fabricating an electromechanical assembly, comprising the steps of:

depositing by a first device a first material into a plurality of stacked regions, each successive region positioned on top of a previously deposited region, the plurality of stacked regions forming a base region comprising one or more void elements;

selecting by a second device two or more module components from a library of module components, each module component comprising one or more connection elements;

positioning by the second device the selected module components into a portion of the one or more void elements of the base region portion such that the selected module components are adjacent to and in direct contact with one another;

connecting directly the one or more connection elements of the adjacent selected module components, the base region portion and the connected adjacent selected module components creating both mechanical properties and electrical properties of the electromechanical assembly.

2. The method for fabricating an electromechanical assembly according to claim 1 wherein the first device is a 3D printing machine.

3. The method for fabricating an electromechanical assembly according to claim 1 wherein the second device is a pick-and-place machine.

4. The method for fabricating an electromechanical assembly according to claim 1 wherein the first material is a photopolymer material.

5. The method for fabricating an electromechanical assembly according to claim 1 wherein each of the two or more selected module components includes an electrical element selected from the group comprising: 2-way connect, 4-way connect, crossover connect, resistor, capacitor, inductor, diode, transistor, switch, and microcontroller.

6. The method for fabricating an electromechanical assembly according to claim 1 wherein the positioning step further comprises a step of applying heat by a third device to fuse the adjacent selected module components to one another.

7. The method for fabricating an electromechanical assembly according to claim 6 wherein the third device is a laser sintering machine.

8. The method for fabricating an electromechanical assembly according to claim 1 wherein each of the two or more selected module components comprises a top surface that includes the one or more connection elements, the connection elements comprising one or more pads.

9. The method for fabricating an electromechanical assembly according to claim 8 wherein each of the two or more selected module components comprises a bottom surface that includes the one or more connection elements, the connection elements comprising one or more pads.

10. The method for fabricating an electromechanical assembly according to claim 9 wherein the one or more pads of the top surface of a first adjacent selected module component connect to the one or more pads of the bottom surface of a second adjacent selected module component.

11. An electromechanical assembly comprising:
a base region portion comprising a first plurality of successive material regions, wherein the first plurality of successive material regions forms one or more void elements;
two or more module components positioned adjacent to and in direct contact with one another in the one or more void elements, each module component comprising one or more connection elements, wherein a first module component is directly connected to the one or more connection elements of a second module component; and
a top region portion comprising a second plurality of successive material regions, wherein the second plurality of successive material regions encapsulates the connected module components.

12. The electromechanical assembly according to claim 11 wherein each of the two or more module component comprises a tile element with an electrical element positioned on a surface or within a surface of the tile element.

13. The electromechanical assembly according to claim 12 wherein the tile element is a rectangular parallelepiped shape.

14. The electromechanical assembly according to claim 13 wherein the tile element is a 3 millimeter (mm) square shape with a thickness of 0.9 millimeters (mm).

15. The electromechanical assembly according to claim 12 wherein the electrical element is selected from the group of electrical elements comprising: 2-way connect, 4-way connect, crossover connect, resistor, capacitor, inductor, diode, transistor, switch, and microcontroller.

16. The electromechanical assembly according to claim 11 wherein each of the one or more connection elements comprises one or more pads on a top surface or a bottom surface of the module component.

17. A system for fabricating an electromechanical assembly, comprising:
a printing apparatus configured to deposit a first material into a first plurality of stacked regions, the first plurality of stacked regions forming a base region portion comprising one or more void elements;
a module library comprising a plurality of module components, each module component comprising one or more connection elements;
a component placement apparatus configured to select from the module library two or more module components, the component placement apparatus further positions the two or more selected module components within the one or more void elements of the base region portion such that the two or more selected module components are adjacent to and in direct contact with one another, and wherein the one or more connection elements of a first selected module component are connected directly to the one or more connection elements of a second selected module component; and
the base region portion and the connected selected module components creating both mechanical properties and electrical properties of the electromechanical assembly.

18. The system for fabricating an electromechanical assembly according to claim 17 further comprising a fusion device configured to fuse the connected selected module components together.

19. The system for fabricating an electromechanical assembly according to claim 18 wherein the fusion device is a laser sintering machine.

20. The system for fabricating an electromechanical assembly according to claim 17 wherein the one or more connection elements comprise one or more pads on a top surface or a bottom surface of each of the two or more selected module components.

21. The system for fabricating an electromechanical assembly according to claim 17, wherein the electrical properties are achieved through direct connections between the one or more connection elements of the connected selected module components without the need for wire or trace.

22. The system for fabricating an electromechanical assembly according to claim 17, wherein the printing apparatus is configured to deposit a second material onto the first plurality of stacked regions to encapsulate the connected selected module components.

23. The system for fabricating an electromechanical assembly according to claim 17, wherein the two or more selected module components comprise a tile element with an electrical element positioned on a surface or within a surface of the tile element.

24. The system for fabricating an electromechanical assembly according to claim 17, wherein the two or more selected module components are prefabricated with the same size and shape, but the electrical properties and the mechanical properties differ between each of the two or more selected module components.

25. The system for fabricating an electromechanical assembly according to claim 17, wherein the two or more selected module components include an electrical element selected from the group consisting of: 2-way connect, 4-way connect, crossover connect, resistor, capacitor, inductor, diode, transistor, switch, and microcontroller.

26. The system for fabricating an electromechanical assembly according to claim 20, further comprising a processor containing instructions that when executed, cause the processor to communicate with a controller such that the controller provides the one or more pads with programming signals to enable the printing apparatus to individually program each of the two or more selected module components.

27. The system for fabricating an electromechanical assembly according to claim 17, wherein the one or more connection elements are one or more of: a pad, a pin-in socket, a rack-and-pinion connection, a captive hinge, or a spring.

* * * * *